(12) United States Patent
Arras et al.

(10) Patent No.: US 10,112,892 B2
(45) Date of Patent: Oct. 30, 2018

(54) PROCESS FOR PREPARING POLYISOCYANATES

(71) Applicant: Covestro Deutschland AG, Leverkusen (DE)

(72) Inventors: Jürgen Arras, Itzehoe (DE); Jan Busch, Düsseldorf (DE); Christian Steffens, Köln (DE); Dietmar Wastian, Dormagen (DE); Manfred Keller-Killewald, Dormagen (DE); Holger Conzelmann, Lichtenwald (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/736,485

(22) PCT Filed: Jun. 27, 2016

(86) PCT No.: PCT/EP2016/064811
§ 371 (c)(1),
(2) Date: Dec. 14, 2017

(87) PCT Pub. No.: WO2017/001322
PCT Pub. Date: Jan. 5, 2017

(65) Prior Publication Data
US 2018/0179150 A1 Jun. 28, 2018

(30) Foreign Application Priority Data
Jun. 29, 2015 (EP) .................................. 15174217

(51) Int. Cl.
C07C 263/10 (2006.01)

(52) U.S. Cl.
CPC .................................. C07C 263/10 (2013.01)

(58) Field of Classification Search
CPC .................................................. C07C 263/10
See application file for complete search history.

(56) References Cited

U.S. PATENT DOCUMENTS

| 3,287,387 A | 11/1966 | Denton et al. |
| 3,544,611 A | 12/1970 | Michelet et al. |
| 3,947,484 A | 3/1976 | Mitrowsky et al. |
| 4,128,569 A * | 12/1978 | Horn .................... C07C 263/10 560/347 |
| 4,289,732 A | 9/1981 | Bauer et al. |
| 4,419,295 A | 12/1983 | Hennig et al. |
| 4,422,976 A | 12/1983 | Yamamoto et al. |
| 4,581,174 A | 4/1986 | Ohlinger et al. |
| 5,117,048 A | 5/1992 | Zaby et al. |
| 5,599,968 A | 2/1997 | Bankwitz et al. |
| 6,576,788 B1 | 6/2003 | Penzel et al. |
| 7,767,160 B2 | 8/2010 | Sasaki et al. |
| 7,851,648 B2 | 12/2010 | Sohn et al. |
| 8,079,752 B2 | 12/2011 | Rausch et al. |
| 8,097,751 B2 | 1/2012 | Koch et al. |

FOREIGN PATENT DOCUMENTS

| DE | 844896 A | 4/1944 |
| DE | 1 037 444 B | 10/1954 |
| DE | 1175666 B | 8/1964 |
| DE | 2058032 A | 5/1972 |
| DE | 300168 A7 | 5/1992 |
| FR | 1126440 A | 11/1956 |
| FR | 2129554 A5 | 10/1972 |
| FR | 2325637 A | 4/1977 |
| GB | 901377 A | 7/1962 |
| GB | 1077031 A | 7/1967 |
| GB | 1173890 A | 12/1969 |
| GB | 1238669 A | 7/1971 |
| GB | 1341311 A | 12/1973 |

OTHER PUBLICATIONS

Plocker, U. et al., Process Analysis and Synthesis: Modeling, Simulation and Optimization, Ch. 9, Chemical Engineering, vol. 2, 5th ed., pp. 270-279, 2004 (English Translation Attached).
Tosum, G., A Study of Micromixing in Tee Mixers, Industrial & Engineering Chemical Research, vol. 26: 1184-1193, 1987 (English Version Attached).
Ullmanns Encyclopedia of Technical Chemistry, 4th ed., vol. 13, pp. 351-353, 1977 (English Translation Attached).

* cited by examiner

*Primary Examiner* — Yevgeny Valenrod
*Assistant Examiner* — Blaine G Doletski
(74) *Attorney, Agent, or Firm* — Donald R. Palladino

(57) ABSTRACT

The present invention relates to a continuous process for preparing a polyisocyanate, in which a polyamine and phosgene are first converted predominantly to carbamoyl chloride and amine hydrochloride and only in minor proportions to polyisocyanate, and a portion of the carbamoyl chloride- and amine hydrochloride-containing reaction mixture thus obtained is recycled into the reaction with phosgene, wherein polyamine, phosgene and the carbamoyl chloride- and amine hydrochloride-containing reaction mixture are mixed intimately in a mixing unit. The portion of the carbamoyl chloride- and amine hydrochloride-containing reaction mixture which is not recycled into the phosgenation is worked up to give the polyisocyanate.

15 Claims, 1 Drawing Sheet

PROCESS FOR PREPARING POLYISOCYANATES

CROSS-REFERENCE TO RELATED APPLICATIONS

This application is a national stage application under 35 U.S.C. § 371 of PCT/EP2016/064811, filed Jun. 27, 2016, which claims the benefit of European Application No. 15174217.8, filed Jun. 29, 2015, both of which are being incorporated by reference herein.

FIELD

The present invention relates to a continuous process for preparing a polyisocyanate, wherein a polyamine and phosgene are firstly reacted to form predominantly carbamoyl chloride and amine hydrochloride and only minor proportions of polyisocyanates and part of the resulting reaction mixture containing carbamoyl chloride and amine hydrochloride is recirculated to the reaction with phosgene, with polyamine, phosgene and the reaction mixture containing carbamoyl chloride and amine hydrochloride being intimately mixed with one another in a mixing device. The part of the reaction mixture containing carbamoyl chloride and amine hydrochloride which is not recirculated to the phosgenation is worked up to give the polyisocyanate.

BACKGROUND

Many processes are known and described in the literature for preparing polyisocyanates by phosgenation of the corresponding amines. Depending on the type of amines, the reaction can be carried out in the gas or liquid phase and batchwise or continuously (W. Siefken, Liebigs Ann. 562, 75-106 (1949)).

The procedure for continuous syntheses of organic isocyanates on an industrial scale has already been described a number of times, see, for example, Ullmanns Encyklopädie der technischen Chemie, 4$^{th}$ edition (1977), volume 13, pp. 351 to 353. Both aromatic isocyanates such as methylenedi (phenyl isocyanate) (hereinafter MMDI—"monomeric MDI"), polymethylene-polyphenylene polyisocyanate (a mixture of MMDI and its higher homologs, hereinafter PMDI, "polymeric MDI") to tolylene diisocyanate (hereinafter TDI) and also aliphatic isocyanates such as hexamethylene diisocyanate (hereinafter HDI) or isophorone diisocyanate (hereinafter IPDI) are used worldwide.

The industrial processes for the production of aromatic isocyanates such as MMDI, PMDI and TDI and of aliphatic isocyanates such as HDI and IPDI are virtually exclusively operated in the continuous mode. DE-A-844 896 may be mentioned as an example of such a process in various continuously operated vessels.

The phosgenation of primary amines ($RNH_2$) is usually carried out in stages, with the carbamoyl chloride (RN-HCOCl) firstly being formed from the starting materials at low temperature and this subsequently being converted at elevated temperature into the corresponding isocyanate (RNCO), and with hydrogen chloride being eliminated in both steps. During the first stage, known as the "cold phosgenation", the amine hydrochloride ("$RNH_2.HCl$"=$RNH_3Cl$) corresponding to the amine used occurs as significant by-product, and this reacts in the "hot phosgenation" in the presence of phosgene to form the corresponding isocyanate. Temperatures below 60° C. are usually employed in the cold phosgenation, while temperatures in the range from 100° C. to 200° C. are attained in the case of the hot phosgenation. Two-stage processes are described, for example, in the documents DE-A-20 58 032, DE-A-21 53 268 and DE-A-1 233 854.

At all temperatures and pressures employed industrially, the reaction between amine and phosgene occurs very quickly in the liquid phase. In order to avoid secondary reactions, the mixing of the reactants should be carried out very effectively. The phosgenation of primary amines in a mixer-reactor as first stage has therefore been disclosed in many publications.

Mixers can be divided into various classes. Apart from dynamic mixers (e.g. stirrers, turbines or rotor-stator systems) and static mixers such as Kenics, Schaschlik or SMV mixers, nozzle mixers are also known (Ind. Eng. Chem. Res. 26, 1987, 1184-1193). For example, pin mixers (EP-A-2 077 150) and Lefos nozzles (EP-A-0 322 647) are particularly suitable for preparing aromatic isocyanates.

A number of apparatuses have been developed for the phosgenation of amines, with these optionally also being able to be used as phase separation vessels. The phosgenation of amines to form the corresponding isocyanates can therefore take place in a stirred vessel (e.g. DE-A 14 68 445), in a cascade of stirred vessels (e.g. DE-C 844 896) or in tube reactors, with the latter being able to be either packed (e.g. WO-A-99/54289) and unpacked (e.g. Ullmanns Encyklopädie der technischen Chemie, 4$^{th}$ edition (1977), volume 13, pp. 351-353). In the case of a reduced reactor volume, circulation reactors with recirculation can also be used to ensure a sufficient residence time for completing the reaction.

The first publication DE-A-1 593 412 fundamentally describes a continuous production process for organic isocyanates, which comprises a "reaction circle" (in the drawing the tube 3 present in the form of a ring conduit) which is followed by the work-up by distillation in a second reaction stage in a column in which the carbamoyl chloride present is converted into the corresponding isocyanate. Apart from MMDI, the preparation of TDI and aliphatic isocyanates was also described. In the reaction circle, the reaction of amine to form carbamoyl chloride is carried out at a pressure of from 10 to 50 atm gauge (about 11 to 51 bar absolute) and a temperature of from 40 to 120° C. The reaction circle is operated with an amine stream being introduced at one point on the ring conduit and a mixture of fresh phosgene and phosgene recovered in the column being introduced at another position on the reaction circle located downstream of the place of introduction of the amine. The starting materials introduced in this way and carbamoyl chloride formed therefrom are circulated in the ring conduit. Part of the circulated reaction mixture is discharged each time unit at a third position on the reaction circle located downstream of the place of introduction of phosgene via a separator integrated into the reaction circle and is fed to the column. The use of a mixing device different from a single tube, in which amine, phosgene and carbamoyl chloride are mixed at the same time, is not disclosed. Phosgene is preferably used in a very large excess, for example from 100 to 500%, probably in order to suppress polymerization reactions. The column mentioned is considered to be an apparatus for dissociating carbamoyl chloride into isocyanate and hydrogen chloride and is operated at a pressure of at least 10 atm gauge (about 11 bar absolute). Below the top of the column, phosgene is recovered in a side offtake stream and is recirculated via a stop vessel into the reaction circle. At the top of the column, a hydrogen chloride condensate (about 10 kg/h) which still contains about 6% of phosgene is obtained via heat exchangers at 82° C. (example 3). The MMDI solution obtained at the bottom at 142° C. is then fed to the solvent rectification column; this stream contains not only MMDI (14.9 kg/h) but also still considerable amounts of phosgene (30 kg/h).

A circulation process with subsequent work-up for the preparation of isocyanates by phosgenation is disclosed in EP 0 716 079 B1. The design of the process advantageously allows the omission of a circulation pump. Excesses of phosgene in the range from 110 to 300% are claimed. The starting materials are fed at separate places into the bubble column, with the phosgene being present in gaseous form and the mixture consisting of MDA and monochlorobenzene being present in liquid form. The reaction solution is continuously circulated by the evolution of hydrogen chloride. The process is operated in a temperature range from 60 to 100° C. and at a pressure of from 0.5 to 5 bar.

A circulation reactor which is operated at pressures of up to 14 kg/cm$^2$ is described by DE-B-1 037 444. Here, amine, phosgene and the inert solvent o-dichlorobenzene are fed into the mixing circle at three different places, with a pump effecting the circulation mode. After the abovementioned streams have been combined, the reaction mixture goes into a heater and temperatures above 110° C. are attained. The mixture is depressurized via a throttle valve and then goes into a collection vessel which is operated under atmospheric pressure. The gaseous materials are taken off at the top of the collection vessel and obtained as a mixture consisting of hydrogen chloride and phosgene via a condenser. At the bottom of said vessel, part of the isocyanate solution is recirculated and the other part is subjected to a further separation operation. Excesses of phosgene of at least 96% are necessary in order to obtain a yield of diphenylmethane 4,4'-diisocyanate of 90.5% in the reactor described at a low gauge pressure of 0.07 kg/cm$^2$.

A two-stage production process for isocyanates is described in DE 32 12 510 C3, with a mixture consisting of isocyanates and the corresponding carbamoyl chloride being recirculated in the presence of phosgene and an inert solvent. The first reaction stage is carried out in a tank-like vessel or in a tubular circulation conduit at temperatures of from 60 to 100° C. and an absolute pressure of from 4 to 8 bar. To complete the conversion of carbamoyl chloride formed as an intermediate, the reaction mixture is fed at the same pressure but at an increased temperature of from 120 to 160° C. into a second stage in order to obtain an isocyanate concentration of from 10 to 25%. Due to the reaction conditions selected, the plant described can advantageously be lined with stainless steel instead of more costly materials. The reaction mixture is present as a slurry (=suspension) in the process described. The excess of phosgene described is at least 100%, and hydrogen chloride is discharged at a maximum of 10.8 bar.

To combine the starting materials with recirculated reaction mixture, DE 26 24 285 C2 describes the use of a motive jet nozzle which advantageously allows intensive mixing in a short time. As a result of the pressure range from 1 to 10 bar employed, not only crude MDI but also a tolylene diisocyanate isomer mixture, naphthalene 1,5-diisocyanate and phenylene 1,4-diisocyanate could be obtained in high yields at residence times of from 10 to 180 minutes. No pressure increase to increase the yield was found, and the excess of phosgene relative to MDA as amine component was greater than 100%.

DE-A-2 252 068 describes a process for the phosgenation of amines to form isocyanates, which is operated without solvent and with recirculation of the isocyanates produced at a pressure of up to 100 atm and a temperature of up to 240° C. in an apparatus. Here, liquefied amine is firstly reacted adiabatically at 100 atm and 150° C. with a mixture consisting of phosgene and recirculated isocyanate in a tube reactor, with a temperature of 240° C. being attained. The reaction mixture is subsequently depressurized isentropically to 20 atm and fresh phosgene/isocyanate mixture is introduced. Apart from isocyanates, hydrogen chloride is obtained at a pressure of 3 atm by work-up of the gaseous components by distillation and phosgene is recirculated in liquid form to the process.

A two-stage process for the production of isocyanate is disclosed by DE-A-2 058 032; here, the temperature is gradually increased during the hot phosgenation. An excess of phosgene of, for example, 8% can be employed here in order to obtain isocyanates in yields in the range from 90 to 95%. This is demonstrated specifically only for the phosgenation of the monofunctional amine aniline. These yields are too low for today's requirements; in addition, it is questionable whether the knowledge disclosed in this document can readily be applied to the phosgenation of polyamines in which there is a risk of polymerization reactions. Particular mention may here be made of the formation of polyureas by polyaddition of polyamines with polyisocyanates. The plant described comprises, as significant part, a mechanically mixed, horizontal tube in which the temperature is gradually increased from 30 to 150° C. and which connects the cold phosgenation part to the degassing tube.

A circulation apparatus for preparing isocyanates, which consist essentially of a circulation conduit, a polyamine/carbamoyl chloride contact unit and a mixing unit for applying shear, is described in EP-A-1 867 632. A distance of 1000 mm and less between contact unit and mixing is claimed. The advantage of the apparatus described is that the formation of ureas as secondary components is reduced by the more effective mixing of the two reactants. Excesses of phosgene of from 0% to 5900% ($2 \leq n(COCl2)/n(polyamine) \leq 60$) are indicated. The subject matter of the invention makes it possible, according to statements in the document, to suppress the formation of urea-like secondary components, which has the effect of increasing the yield of polyisocyanate. However, examples which could demonstrate the advantage claimed are not described in the application. In particular, there is no evidence that industrially acceptable yields are achieved even at low or no excesses of phosgene. A distance of 1000 mm or less between contact unit and mixing unit is claimed; the feed streams are introduced at a linear velocity of from 0.5 to 10 m/s into the reaction solution (0.3 to 5 m/s) via tubes. Shape and construction are indicated as drawing in the application. Furthermore, it is said in the description of the application that the formation of carbamoyl chlorides and polyisocyanates is minimized by reaction of HCl with polyamine to form polyamine hydrochloride. Due to generation of a laminar flow profile, no reaction takes place in the circulation conduit.

A further process for preparing isocyanates is disclosed in EP 0 150 435 B1. Here, hydrogen chloride is separated off before the circulation of the reaction mixture present in the circuit in order to obtain concentrations below 0.5% by weight before the addition of amine. Intermediate salt formation and by-product formation is advantageously suppressed in this process by the removal of the hydrogen chloride and, as a result, the isocyanate concentration in the reactor is increased. The molar ratio of phosgene to amine groups is from 12:1 to 200:1. The hydrogen chloride gas which has been separated off is obtained under a high pressure. The reactants are mixed by means of a motive jet nozzle with the recycle stream, which is mainly isocyanate dissolved in monochlorobenzene, with a temperature of 130° C. and a pressure of 14.5 bar prevailing in the mixing circle. A column is used to separate hydrogen chloride and phosgene, with the phosgene obtained at the bottom being recirculated to the process.

It is common to all the above-described processes that in practice they require very large excesses of phosgene in order to achieve very good yields of polyisocyanates. Particularly in the case of the preparation of MMDI and PMDI, a high excess of phosgene is indispensable in the prior art in order to achieve acceptable yields (which in industrial production should be >99% for economic reasons). However, high excesses of phosgene are not very desirable both for economic reasons and for safety reasons. There was therefore a need for a process for the production of polyisocyanates, in which the excess of phosgene can be kept low without this resulting in other disadvantages (such as reduced yield or increased polymerization tendency with the associated risk of the formation of deposits).

SUMMARY

Taking into account what has been said above, the present invention provides a continuous process for preparing a polyisocyanate in the liquid phase by reaction of the corresponding polyamine with phosgene, with the corresponding carbamoyl chloride and the corresponding amine hydrochloride occurring as intermediates, wherein (i) a phosgene-containing stream (1), a polyamine-containing stream (2) and a stream (3) containing carbamoyl chloride and amine hydrochloride are mixed in a mixing device (1000), where phosgene is used in a stoichiometric excess of from >0% to 50% of theory, preferably from >0% to 20% of theory, particularly preferably from >0% to 15% of theory, very particularly preferably from >0% to 10% of theory, based on the amine groups of the polyamine present in stream (2)

(ii) the mixed stream (4) obtained in step (i) is conveyed through a reactor (2000) in which an absolute pressure of from 20 bar to 60 bar and a temperature of from 80° C. to 200° C., preferably an absolute pressure of from 20 bar to 55 bar and a temperature of from 80° C. to 170° C., particularly preferably an absolute pressure of from 20 bar to 50 bar and a temperature of from 80° C. to 150° C., prevail, so that the polyamine used is largely to completely, preferably completely, reacted, forming a stream (5) containing carbamoyl chloride and amine hydrochloride (iii) a gaseous purge stream is optionally discharged from the stream (5) containing carbamoyl chloride and amine hydrochloride which is formed in step (ii), giving a stream (6) which contains carbamoyl chloride and amine hydrochloride and has been depleted in gaseous components, (iv) the stream (5) obtained in step (ii) or the stream (6) obtained in step (iii) is divided into two substreams (7, 8), where
  (a) the substream (7) is used as stream (3) containing carbamoyl chloride and amine hydrochloride in step (i) and
  (b) the substream (8) is converted into the desired polyisocyanate.

DETAILED DESCRIPTION

Figure 1:
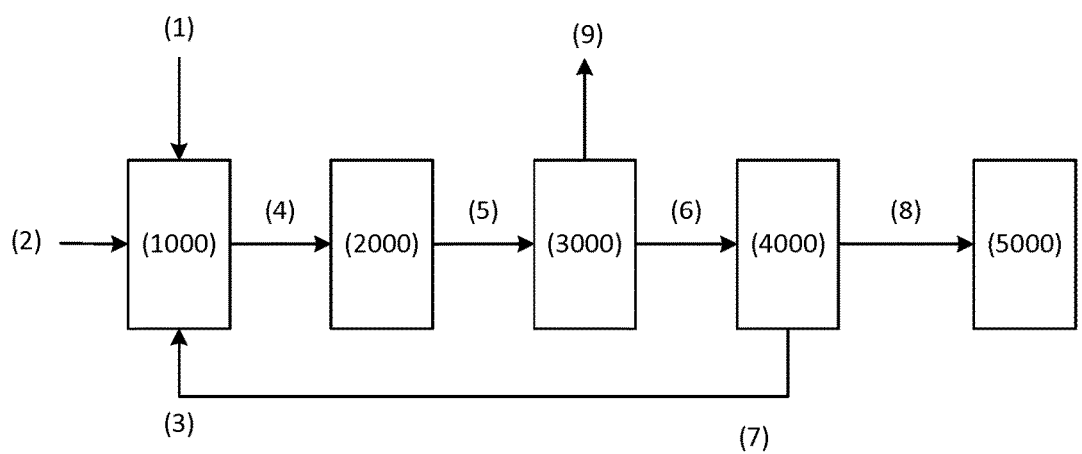
FIG. 1 schematically illustrates an embodiment of the process of the invention.

For the purposes of the present invention, the terms carbamoyl chloride and amine hydrochloride are used regardless of whether only one or all amine functions —NH$_2$ of the starting polyamine have been converted into —NHCOCl or —NH$_3$Cl.

For the purposes of the present invention, polyamines and polyisocyanates are materials which contain at least two amine groups or isocyanate groups, respectively.

A "mixing device (1000)" is, for the purposes of the present invention, a device which is specifically constructed for mixing a plurality of streams (see below for details).

For the purposes of the present invention, the word "a" in connection with enumerable parameters is to be understood as number-indicating word and not merely as indefinite article only when this is expressly stated or is clear from the context. For example, the expression "a reactor" also encompasses embodiments in which a plurality of reactors are connected in parallel or in series.

Embodiments of the invention will be described in more detail below. Here, various embodiments can be combined with one another in any way as long as the contrary is not clear to a person skilled in the art from the context.

The invention is concerned with a continuous process carried out industrially for the synthesis of polyisocyanates. At the beginning of such a process, for example when restarting a plant after a production downtime, there is naturally not yet any stream (3) containing carbamoyl chloride and amine hydrochloride. The reaction of polyamine and phosgene is therefore initially carried out without addition of this stream. As soon as a stable operating state of the continuous production process has been attained, the process is operated as described above, i.e. with introduction of the stream (3).

The process of the invention is suitable for, for example, the preparation of methylenedi(phenyl diisocyanate) (MMDI) as pure isomers or as isomer mixture, polymethylenepolyphenyl polyisocyanate (PMDI), mixtures of methylenedi(phenyl isocyanate) and polymethylenepolyphenyl polyisocyanate, tolylene diisocyanate (TDI) as pure isomers or isomer mixture, isomers of xylylene diisocyanate (XDI), isomers of diisocyanatobenzene, xylene 2,6-diisocyanate, naphthalene 1,5-diisocyanate (1,5-NDI), diisocyanates based on aliphatic or cycloaliphatic hydrocarbons having from 2 to 18 carbon atoms, e.g. butane 1,4-diisocyanate, pentane 1,5-diisocyanate, hexane 1,6-diisocyanate (HDI), octane 1,8-diisocyanate, nonane 1,9-diisocyanate, decane 1,10-diisocyanate, 2,2-dimethylpentane 1,5-diisocyanate, 2-methylpentane 1,5-diisocyanate (MPDI), 2,4,4 (or 2,2,4)-trimethylhexane 1,6-diisocyanate (TMDI), cyclohexane 1,3- and 1,4-diisocyanate, 1-isocyanato-3,3,5-trimethyl-1-5-isocyanatomethylcyclohexane (IPDI), 2,4- or 2,6-diisocyanato-1-methylcyclohexane (H6-TDI), 1-isocyanato-1-methyl-4 (3)-isocyanatomethylcyclohexane (AMCI), 1,3 (and/or 1,4)-bis(isocyanatomethyl)cyclohexane, bis(isocyanatomethyl) norbornane (NBDI), 4,4' (and/or 2,4)-diisocyanatodicyclohexylmethane, and (cyclo)aliphatic triisocyanates having up to 22 carbon atoms, e.g. triisocyanatocyclohexane, tris(isocyanatomethyl)cyclohexane, triisocyanatomethylcyclohexane, 1,8-diisocyanato-4-(isocyanatomethypoctane, undecane 1,6,11-triisocyanate, 1,7- siisocyanato-4-(4-isocyanatopropyl)heptane, 1,6-diisocyanato-3-(isocyanatomethyl)hexane or 1,3,5-tris (isocyanatomethyl)cyclohexane.

The amines corresponding to the above polyisocyanates are aromatic polyamines such as methylenedi(phenylamine) (MMDA) as pure isomers or as isomer mixture, polymethylenepolyphenylpolyamine (PMDA), mixtures of methylenedi(phenylamine) and polymethylenepolyphenylpolyamine, tolylenediamine (TDA) as pure isomers or isomer mixture, isomers of xylylenediamine (XDA), isomers of diaminobenzene, 2,6-xylidine, 1,5-naphthylenediamine (1,5-NDA), polyamines based on aliphatic or cycloaliphatic hydrocarbons having from 2 to 18 carbon atoms, e.g. 1,4-diaminobutane, 1,5-diaminopentane, 1,6-diaminohexane (HDA), 1,8-diaminooctane, 1,9-diaminononane, 1,10-diaminodecane, 2,2-dimethyl-1,5-diaminopentane, 2-methyl-1,5 -pentanediamine (MPDA), 2,4,4 (or 2,2,4)-trimethyl-1, 6-diaminohexane (TMDA), 1,3- and 1,4-diaminocyclohexane, 1-amino-3,3,5-trimethyl-5-aminomethylcyclohexane (IPDA), 2,4-, or 2,6-diamino-1-methylcyclohexane (H6-TDA), 1 -amino-1-methyl-4-(3)-aminomethylcyclohexane (AMCA), 1,3 (and/or 1,4)-bis (aminomethyl)cyclohexane, bis(aminomethyl)norbornane (NBDA), 4,4' (and/or 2,4')-diaminodicyclohexylmethane, (cyclo)aliphatic polyamines having up to 22 carbon atoms, e.g. triaminocyclohexane, tris(aminomethyl)cyclohexane, triaminomethylcyclohexane, 1,8-diamino-4-(aminomethyl) octane, 1,6,11-undecanetriamine, 1,7-diamino-4-(3-aminopropyl)heptane, 1,6-diamino-3-(aminomethyl)hexane or 1,3,5-tris(aminomethyl)cyclohexane.

The process of the invention is particularly suitable for preparing methylenedi(phenyl isocyanate) (MMDI) as pure isomers or as isomer mixture, polymethylenepolyphenyl polyisocyanate (PMDI), mixtures of methylenedi(phenyl isocyanate) and polymethylenepolyphenyl polyisocyanate, tolylene diisocyanate (TDI) as pure isomers or isomer mixtures, isomers of xylylene diisocyanate (XDI), isomers of diisocyanatobenzene, xylene 2,6-diisocyanate, naphthalene 1,5-diisocyanate (1,5-NDI).

In a particularly preferred embodiment, the present invention provides a process for preparing diphenylmethane diisocyanate (MMDI) and/or polyphenyl-polymethylene polyisocyanate (PMDI). MMDI and PMDI are also referred to collectively as MDI in the context of the present invention, regardless of the degree of polymerization and isomer distribution; an analogous situation applies to MDA.

The preparation of the corresponding polyamines is adequately known from the prior art and will therefore not be described in detail at this point. In the case of the particularly preferred polyisocyanate MDI, the corresponding polyamine MDA is obtained by acid-catalyzed condensation of aniline and formaldehyde. This gives a mixture of the "two-ring compound" MMDA (containing two benzene rings each having an amino group) and higher homologs PMDA ("multiring compounds", containing three or more benzene rings each having an amino group). In most of the processes which are customary in industry, this mixture is phosgenated without prior separation into monomeric and polymeric constituents. A separation into monomeric constituents and polymeric constituents therefore usually takes place only at the stage of the polyisocyanate. This gives firstly the two-ring compound (MMDI) and secondly a mixture of the two-ring compound (MMDI) and the higher homologs (PMDI).

In step (i) of the process of the invention, the starting materials polyamine and phosgene are preferably used in a solvent which is inert under the reaction conditions. Particular preference is given to a process in which the phosgene-containing stream (1) comprises a proportion by mass of from 10% to 90%, preferably from 30% to 70%, particularly preferably from 55% to 65%, of phosgene and a proportion by mass of from 90% to 10%, preferably from 70% to 30%, particularly preferably from 45% to 35%, of an inert solvent, in each case based on the total mass of the stream (1), the polyamine-containing stream (2) comprises a proportion by mass of from 10% to 50%, preferably from 30% to 45%, particularly preferably from 35% to 40%, of polyamine and a proportion by mass of from 90% to 50%, preferably from 65% to 70%, particularly preferably from 60% to 65%, of an inert solvent, in each case based on the total mass of the stream (2).

Inert under the reaction conditions here means that the solvent does not react to a significant extent with the starting materials, intermediates and end products of the reaction. For this reason, the inert solvent for stream (1) and stream (2) is preferably selected independently from among chlorobenzene, dichlorobenzene, toluene, dioxane, dimethyl sulfoxide or a mixture of two or more of the abovementioned solvents. Chlorobenzene and dichlorobenzene are particularly preferred for both streams (1) and (2), with very particular preference being given to chlorobenzene. In the case of the dichlorobenzene, the ortho isomer (ortho-dichlorobenzene) is particularly preferred.

The mixing device used in step (i) has to allow simultaneous mixing of three process streams (carbamoyl chloride/amine hydrochloride, polyamine and phosgene-containing streams (3), (2) and (1)), and the mixing device should be configured so that only two streams (polyamine- and phosgene-containing stream (2) and (1)) can be mixed with one another at times (e.g. during restarting of a production plant after a downtime).

The process streams (1), (2) and (3) to be mixed should preferably be intimately mixed with one another quickly without an appreciable residence section, so that a high product yield is made possible. Mixing of the components in a simple tube does not meet these requirements. This prerequisite is satisfied by many mixing apparatuses described in the literature. These include firstly particular types of static mixers and here particularly nozzles, for example annular slit nozzles (DE-A-1792660), annular hole nozzles (DE-C1-3744001), smooth jet mixing nozzles (EP-A1-0 065 727), fan jet nozzles (DE-A1-2950216), angled jet chamber nozzles (DD-A7-300.168), three-fluid nozzles (DD-A1-132340), countercurrent mixing chambers (DE-B-1146872), banking-up nozzles (FR-E-69428) and Venturi mixing nozzles (DE-B-1175666). Secondly, dynamic mixers which satisfy this prerequisite have been described. These are, inter alia, rotor-stator or turbine-like systems in which the reactants are introduced in concurrent into the mixing unit. An example which may be mentioned is EP-A-2 077 150. Dynamic mixers are preferably used in the process of the invention because the primary mixing both of the starting materials (phosgene- and polyamine-containing streams (1) and (2)) and also the recycle stream (3) which contains carbamoyl chloride and possibly amine hydrochloride and acts as diluent has been found to be particularly effective. Mixing apparatuses which provide a high energy influence required for mixing even at differences in the viscosity ratio $\eta'$ of amine solution (2) to phosgene solution (1), $\eta'=\eta(2)/\eta(1)$, of both less than 0.5 and also greater than 2 (EP 2 077 150 A1) have been found to be particularly advantageous for the preparation of polyisocyanates from the corresponding polyamines by means of phosgenation, which can be considered to be a reaction which starts quickly.

In the reaction of polyamines with phosgene, not only the selectivity to the desired carbamoyl chloride but also the space-time yield of the process are reduced by the (unavoidable) formation of amine hydrochloride particles as by-product. In the prior art, it is usual to react the amine hydrochloride particles formed in-situ at elevated temperatures with a very large excess of phosgene in order to increase the yield. The rate of the reaction is, as described in the literature, determined primarily by the average particle size which can, depending on the quality of mixing at the beginning of the reaction, range from the nanometer range through the micron range to the millimeter range. A more finely particulate dispersion is obtained with an increasing degree of mixing quality. Tubes for amine solution or phosgene solution which introduce the two starting materials into the reaction circle, as are described in the first publication DE-A-1 593 412 perform the mixing task only unsatisfactorily, with the associated disadvantage of the necessity of using a high excess of phosgene in order to complete the reaction of the amine to form the desired carbamoyl chloride.

It has now been found that the continuous phosgenation of polyamines with recirculation of a stream containing carbamoyl chloride and amine hydrochloride can be carried out at a significantly lower excess of phosgene than is described in the literature when using mixing apparatuses of the static or dynamic type.

As reactor in step (ii), it is in principle possible to use any phosgenation reactor known from the prior art. Preference is given to using upright tube reactors through which flow occurs from below. To narrow the residence time, the tube reactor can be segmented by means of suitable internals known to those skilled in the art.

In the reactor (2000), the polyamine is converted into carbamoyl chloride and amine hydrochloride. The formation of polyisocyanate in this stage can naturally not be ruled out entirely, but, as a result of the high pressure to be employed according to the invention in step (ii), generally occurs to only a minor extent. Suitable selection of the reaction conditions (see below for details) makes it possible to shift the ratio of carbamoyl chloride to amine hydrochloride in favor of the former, which is desirable because the phosgenation of amine hydrochloride is, on the basis of experience, a slow reaction. However, the presence of amine hydrochloride in stream (5) cannot be avoided completely.

In one embodiment of the process of the invention, the reactor (2000) is operated adiabatically, i.e. without deliberate introduction or removal of heat. In such a process, the enthalpy of reaction is, disregarding unavoidable heat losses, reflected quantitatively in the temperature difference between inlet stream and outlet stream. To avoid heat losses, the reactor is preferably insulated. The document EP 1 616 857 A1 describes the adiabatic mode of operation in polyamine phosgenation in more detail, in particular in paragraphs [0014] to [0018].

In another embodiment of the process of the invention, the reactor (2000) is operated isothermally, i.e. with introduction of heat via a thermostatable reactor by means of a suitable heat transfer medium (e.g. heat transfer oil, salt milk). The documents DE 1768439 A1, in particular paragraph [0003] on page 8, and EP 1 616 857 B1, in particular paragraphs [0021] to [0022], may be mentioned as examples of the phosgenation of polyamines in an isothermal mode of operation.

Regardless of whether the reactor (2000) is operated adiabatically or isothermally, the reaction is preferably carried out in such a way that the ratio n of the molar amounts of carbamoyl chloride (CSC) and amine hydrochloride (AHC) to polyisocyanate (PIC), $n'=[n(CSC)+n(AHC)]/n(PIC)$, in the product stream (5) leaving the reactor 2000 is from 2:1 to 100:1, preferably from 10:1 to 80:1, particularly preferably from 30:1 to 60:1. These molar ratios are preferably set by suitable selection of the absolute pressure prevailing in (2000) and can be calculated by a person skilled in the art under known boundary conditions. A higher pressure in (2000) leads to the proportion of dissolved hydrogen chloride increasing, so that the equilibrium between polyisocyanate and carbamoyl chloride or amine hydrochloride is shifted in the direction of the carbamoyl chloride or amine hydrochloride. A generalization of the dependence of the molar ratio n on the absolute pressure in (2000) is difficult because of the variety of dependences on the other boundary conditions. However, a person skilled in the art is able, as a function of the polyamine used, the temperature and the other boundary conditions prevailing in a given production plant, to quantify the relationship between absolute pressure in (2000) and the molar ratio of carbamoyl chloride to polyisocyanate in the product stream (5) leaving the reactor (2000) by means of simple preliminary experiments and/or mathematical simulations.

In step (iii) a gaseous purge stream (9) is optionally discharged from the stream (5) containing carbamoyl chloride and amine hydrochloride which is formed in step (iii) in the reactor (2000) giving a stream (6) which contains carbamoyl chloride and amine hydrochloride and is depleted in gaseous components. This occurs in apparatuses (3000) known from the prior art, for example gas-liquid separators or columns. The apparatus (3000) used for taking off the gaseous purge stream can also be integrated into the reactor (2000). The amount of gaseous purge stream which is optionally discharged in step (iii) preferably corresponds to from >0 to <1.0% by mass of the stream (5) containing carbamoyl chloride and amine hydrochloride, based on the total mass of this stream.

In step (iv), either the stream (5) obtained in step (iii) (in the embodiment without (iii)) or the stream (6) obtained in step (iii) (in the embodiment with step (iii)) is divided into two substreams (7, 8). In a preferred embodiment, stream (7) comprises from 5.0% by mass to 95% by mass and stream (8) comprises from 5.0% by mass to 95% by mass of the stream (5) obtained in step (iii) [in the embodiment without step (iii)] or of the stream (6) obtained in step (iii) [in the embodiment with step (iii)], in each case based on the total mass of the stream (5) or (6).

The substream (7) is recirculated to the reaction (reaction circuit), specifically as stream (3) in step (i) (step (iv) (a)).

The substream (8) is, as explained in more detail below, worked up to give the desired polyisocyanate (10) (step (iv) (b)).

Particularly when the stream (8) contains relatively large amounts of amine hydrochloride, the stream (8) is preferably firstly conveyed through a further reactor (5100) which is operated isothermally. Relatively large amounts of amine hydrochloride are indicated by clouding of the reaction solution. This can in the simplest case be detected by visual observation by means of a sight glass. In the reactor (5100), amine hydrochloride is phosgenated. The product stream taken from the reactor (5100) is then conveyed through a cascade of separators with gradually decreasing pressure. Here, carbamoyl chloride is converted by depressurization into polyisocyanate and excess phosgene is separated off with the gas phase. To avoid a significant reduction in the operating temperature of the individual apparatuses during depressurization, the pressure and temperature range is set in such a way that solids formation is not to be expected during operation. For example, the absolute pressure can be reduced in two stages starting from the pressure and temperature conditions prevailing in the reactor (5100) via an intermediate stage at 12 bar/100° C. to ambient pressure and temperature.

Depending on the precise configuration of the reaction circuit, in particular the operation of the reactor (2000), the reactor (5100) can be omitted and the stream (8) can be conveyed directly through a cascade of separators with gradually decreasing pressure. The omission of the reactor (5100) is made possible by virtually complete reaction of amine hydrochloride in the reactor (2000), which can, in particular, be achieved when (2000) is operated isothermally and not adiabatically. The average residence time in the first reactor also influences the amine hydrochloride content of stream (8). In the case of an increased reactor volume for (2000) and a resulting increase in the average residence time, the reaction of the amine hydrochloride will proceed more completely.

The addition of further phosgene in step (v) (b) is unnecessary in the process of the invention, regardless of whether the reactor (5100) is used or not. Since only small excesses of phosgene are used in the reactor (2000), there is thus overall a far lower phosgene requirement compared to conventional industrial processes. This is highly desirable for safety reasons and also for economic reasons. Excellent yields are obtained by means of the process of the invention despite the lower excesses of phosgene. A further advantage of the process of the invention is that, as a result of the smaller excesses of phosgene, the work-up is simplified, as is described below.

The crude polyisocyanate stream (10) obtained in this way can in principle be worked up to give pure polyisocyanate by all methods known from the prior art. This is achieved, for example, by means of a cascade of rectification columns. However, this rectification sequence is simplified in the process of the invention compared to the prior art by the fact that a significantly smaller amount of phosgene, which for economic reasons is to be made available to the process again, has to be recirculated due to a smaller excess of phosgene. Process stages for liquefaction and/or for dissolution of the excess phosgene in a solvent (phosgene absorption) can thus be made considerably smaller or even be dispensed with entirely, which appreciably reduces the capital costs for construction of a corresponding plant. In the ideal case, the excess of phosgene is so small that the small amounts of unreacted phosgene arising do not have to be recovered in a complicated manner, for example by absorption of phosgene in chlorobenzene as absorption medium at temperatures below 0° C., as is customary in the processes of the prior art. Rather, this recovery of phosgene can be carried out by simple condensation with indirect cooling in the process of the invention. Recovered phosgene can be used as constituent of stream (1) in step (i) or be passed to another use for phosgene. In an alternative embodiment, the residual phosgene is destroyed since the amounts arising are in the most favorable case so small that reuse as material is not absolutely necessary in terms of economics.

Embodiments of the present invention will be explained in more detail with the aid of the accompanying drawings.

FIG. 1 schematically shows, in greatly simplified form, an embodiment of the process of the invention:

a phosgene stream (1), a polyamide stream (2) and a stream (3) containing carbamoyl chloride and amine hydrochloride are fed to a mixing device (1000) and intimately mixed there (step (i) of the process of the invention), with all three streams containing an inert solvent. The resulting mixed stream (4) is conveyed through the reactor (2000) in which the polyamine is reacted so as to form a stream (5) containing carbamoyl chloride and amine hydrochloride (step (ii) of the process of the invention). In a downstream apparatus (3000), a gaseous purge stream (9) comprising predominantly hydrogen chloride is taken off (step (iii) of the process of the invention). The remaining liquid stream (6) is divided into two substreams (7) and (8) in an apparatus (4000) (step (iv) of the process of the invention). Stream (7) is recirculated as stream (3) containing carbamoyl chloride and amine hydrochloride into the mixing device (1000) (step (iv) (a) of the process of the invention), while stream (8) is worked up in (5000) to give the polyisocyanate (10) (step (iv) (b) of the process of the invention).

Figure 2:
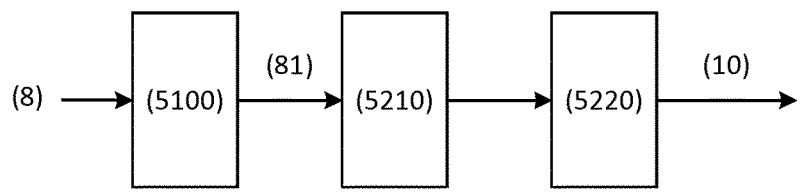
FIG. 2 schematically illustrates an embodiment of the reaction of the carbamoyl chloride and amino hydrochloride present in stream (8) carried out in (5000) to give the polyisocyanate in stream (10).

FIG. 2 shows one possible embodiment of the reaction of the carbamoyl chloride and amine hydrochloride present in stream (8) carried out in (5000) to give the polyisocyanate in stream (10):

stream (8) is firstly fed into an isothermally operated reactor (5100) (step (iv) (b) (1)), and the stream (81) leaving the reactor is conveyed through a cascade (5220) of separators (5210, 5220) with gradually decreasing pressure (step (iv) (b) (2)). The embodiment with two separators (5210, 5220) shown in the figure should be interpreted as illustrative. After passing through the last separator (5220), a polyisocyanate stream (10) which no longer contains any appreciable amount of amine hydrochloride is obtained and this is worked up by a process according to the prior art to give pure polyisocyanate, with the solvent used being recovered (not shown in FIG. 2). Small amounts of CSC may still be present in the polyisocyanate stream (10) and these are dissociated to give polyisocyanate in the further work-up.

EXAMPLES

The examples presented below are based on a process simulation of steady state operation, as described, for example, in U. Plöcker, R. Janowsky, H. Briesen, W. Marquardt, "Prozessanalyse und -synthese: Modeillierung, Simulation und Optimierung", chapter 9 "Stationäre und dynamische Prozesssimulation" "Chemische Technik", Winnacker, Küchler (editors), volume 2, $5^{th}$ edition, Wiley-VCH-Verlag, Weinheim, 2004, pages 270-279 in terms of its significant steps. To calculate the steady state of operation, firstly the phase equilibrium of the individual components and secondly the reaction kinetics of the reaction of MDA with phosgene with adherence to the energy balance and mass balance were used as bases for the model.

Example 1

According to the Invention, Adiabatic Mode of Operation in Reactor (2000), Isothermally Operated After-Reactor (5100)

In a mixing device, 5 kg/h of 4,4'-diaminodiphenylmethane (MMDA) as 41.7 percent by mass solution in ortho-dichlorobenzene (stream (2)), 5.3 kg/h of phosgene as 58 percent by mass solution in ortho-dichlorobenzene (stream (1)) were combined with a recirculated stream containing carbamic acid of 37.6 kg/h (stream (3)), with the concentration of carbamoyl chloride being about 25% in ortho-dichlorobenzene. A molar excess of phosgene over the amine used of 5% of theory was set here (step (i) of the process of the invention). The temperature at the outlet of the mixing device was 131° C., and a pressure of 40 bar above atmospheric pressure prevailed. The reaction mixture (stream (4)) subsequently went into a tower-like reactor ((2000), step (ii) on the process of the invention) from which 600 g/h of hydrogen chloride was taken off as gaseous component at the top in order to avoid thermal expansions (step (iii) of the process of the invention). The remaining liquid stream (stream (6)) was subsequently divided in a mass ratio of 1.85:1 into two streams at a temperature of 105° C. (step (iv) of the process of the invention), with 20.2 kg/h (stream (8)) of the stream being fed into an after-reactor (5100) (step (iv) (b) (1) of the process of the invention). The other part (stream (7)) of the stream was recirculated as described above to the mixing device (step (iv) (a) of the process of the invention). In the after-reactor, the stream (8) was heated to 140° C., and the pressure was 40 bar above atmospheric pressure. The pressure was subsequently reduced from 40 bar above atmospheric pressure to ambient atmospheric pressure by means of a plurality of separators (step (iv) (b) (2) of the process of the invention). The liquid crude MMDI solution obtained, which no longer contained any MMDA and had a content of secondary components containing urea groups of 0.5% by mass, based on the mass of the MMDI present in the crude MMDI solution, was purified further by distillation according to the prior art, with the solvent being recovered.

Example 2

According to the Invention, Isothermal Mode of Operation in Reactor (2000) without After-Reactor 5 kg/h of 4,4'-diaminodiphenylmethane as 42 percent by mass solution in ortho-dichlorobenzene (stream (2)) together with 9.5 kg/h of phosgene as 54 percent by mass solution in ortho-dichlorobenzene (stream (1)) were combined with a recirculated stream containing carbamic acid of 23.8 kg/h (stream (3)) in a mixing device, with the concentration of carbamoyl chloride being about 39% in ortho-dichlorobenzene. A molar excess of phosgene over the amine used of 5% of theory was set here (step (i) of the process of the invention). The temperature at the outlet of the mixing device was 139° C., and a pressure of 40 bar above atmospheric pressure prevailed. The reaction mixture subsequently went into a heatable tower-like reactor ((2000); step (ii) of the process of the invention) from which 600 g/h of hydrogen chloride as gaseous component were taken off at the top in order to avoid thermal expansions (step (iii) of the process of the invention). The remaining liquid stream (stream (6)) was subsequently divided in a mass ratio of 1.22:1 into two streams at a temperature of 140° C. (step (iv) of the process of the invention), and 19.5 kg/h (stream (8)) of the stream were let down to ambient atmospheric pressure by means of a plurality of separators (step (iv) (b) of the process of the invention). The other part of the stream is recirculated as described above into the mixing device (step (iv) (a) of the process of the invention). The liquid crude MMDI solution obtained after passing through the separators, which no longer contained any MMDA and had a content of secondary components containing urea groups of 1.4%, based on the mass of the MMDI present in the crude MMDI solution, was purified further by distillation according to the prior art, with the solvent being recovered.

Example 3

Comparative Example

Example 3 of DE-A 1593412 is employed as comparison.

The comparative example gave, at an excess of phosgene of 280% of theory, a yield of MMDI of 94%. In examples 1 and 2, the yield of MMDI was reduced merely by the secondary components containing urea groups. Since the content of these secondary components which reduced the quality of the MMDI is in a comparable range to that in MMDI prepared in a conventional way corresponding to the prior art, an advantage in respect of safety and economics is achieved by the lower excess of phosgene and the smaller amount of solvent.

The invention claimed is:

1. A continuous process for liquid phase preparation of a polyisocyanate by reaction of a corresponding polyamine with phosgene, with a corresponding carbamoyl chloride and a corresponding amine hydrochloride occurring as intermediates, comprising:
   (i) mixing a phosgene-containing stream, a polyamine-containing stream and a stream containing carbamoyl chloride and amine hydrochloride in a mixing device to obtain a mixed stream, where phosgene is used in a stoichiometric excess of from >0% to 50% of theory, based on the amine groups of the polyamine present in the polyamine-containing stream;
   (ii) conveying the mixed stream obtained in step (i) through a reactor in which an absolute pressure of from 20 bar to 60 bar and a temperature of from 80° C. to 200° C., prevail, thereby forming a stream containing carbamoyl chloride and amine hydrochloride;
   (iii) optionally discharging a gaseous purge stream from the stream containing carbamoyl chloride and amine hydrochloride which is formed in step (ii), giving a stream which contains carbamoyl chloride and amine hydrochloride and has been depleted in gaseous components, and
   (iv) dividing the stream containing carbamoyl chloride obtained in step (ii) or the stream contains carbamoyl chloride and amine hydrochloride and has been depleted in gaseous components obtained in step (iii) into two substreams, where
      (a) one substream is used as the stream containing carbamoyl chloride and amine hydrochloride in step (i) and
      (b) the other substream converted into the desired polyisocyanate.

2. The process of claim 1, wherein the reactor in step (ii) is operated adiabatically.

3. The process of claim 1, wherein the reactor in step (ii) is operated isothermally.

4. The process of claim 1, wherein, in step (iv) (b), the other substream is converted into the desired polyisocyanate by a process comprising:
   (1) conveying the substream through an isothermally operated reactor and then
   (2) through a cascade of separators with gradually decreasing pressure.

5. The process of claim 3, wherein, in step (iv) (b), the other substream is conveyed directly through a cascade of separators with gradually decreasing pressure.

6. The process of claim 1, wherein step (iv) (b) is carried out without addition of phosgene.

7. The process of claim 1, wherein
the phosgene-containing stream comprises a proportion by mass of from 10% to 90% of phosgene and a proportion by mass of from 90% to 10% of an inert solvent, in each case based on the total mass of the stream,
the polyamine-containing stream comprises a proportion by mass of from 10% to 50% of polyamine and a proportion by mass of from 90% to 50% of an inert solvent, in each case based on the total mass of the stream.

8. The process of claim 7, wherein the inert solvent in the phosgene-containing stream and in the polyamine-containing stream is selected independently from the group of chlorobenzene, dichlorobenzene, toluene, dioxane, dimethyl sulfoxide and a mixture of two or more of the abovementioned solvents.

9. The process of claim 1, wherein the stream containing carbamoyl chloride and amino hydrochloride comprises a ratio of the molar amount of carbamoyl chloride and amine hydrochloride to polyisocyanate of from 2:1 to 100:1.

10. The process of claim 1, wherein the mixing device used in step (i) is a dynamic mixer.

11. The process of claim 1, wherein, in step (i), phosgene is used in a stoichiometric excess of from >0% to 20% of theory, based on the amine groups of the polyamine present in the polyamine-containing stream.

12. The process of claim 11, wherein, in step (i), phosgene is used in a stoichiometric excess of from >0% to 15% of theory, based on the amine groups of the polyamine present in the polyamine-containing stream.

13. The process of claim 12, wherein, in step (i), phosgene is used in a stoichiometric excess of from >0% to 10% of theory, based on the amine groups of the polyamine present in polyamine-containing stream.

14. The process of claim 1, wherein unreacted phosgene is recovered by means of condensation by indirect cooling.

15. The process of claim 1, wherein the isocyanate is selected from the group consisting of methylenedi(phenyl isocyanate) as pure isomer or as isomer mixture, polymethylenepolyphenyl polyisocyanate, mixtures of methylenedi(phenyl diisocyanate) and polymethylenepolyphenyl polyisocyanate, tolylene diisocyanate as pure isomer or isomer mixture; isomers of xylylene diisocyanate, isomers of diisocyanatobenzene, xylene 2,6-diisocyanate and naphthalene 1,5-diisocyanate.

* * * * *